United States Patent [19]
Nunokawa

[11] Patent Number: 5,643,340
[45] Date of Patent: Jul. 1, 1997

[54] SYNTHETIC VASCULAR PROSTHESIS

[76] Inventor: Mioko Nunokawa, 35-5-203, Tomigaya 1-chome, Shibuya-ku, Tokyo, Japan

[21] Appl. No.: 548,859

[22] Filed: Oct. 26, 1995

[30] Foreign Application Priority Data

Oct. 27, 1994 [JP] Japan .................. 6-264205

[51] Int. Cl.⁶ .................................................. A61F 2/06
[52] U.S. Cl. ................................................ 623/1; 606/153
[58] Field of Search ...................... 623/1, 12; 606/153, 606/108, 191, 198, 155, 156

[56] References Cited

U.S. PATENT DOCUMENTS

| | | | |
|---|---|---|---|
| 3,713,441 | 1/1973 | Thomas | 606/153 X |
| 4,047,252 | 9/1977 | Liebig et al. | |
| 4,321,711 | 3/1982 | Mano | |
| 4,497,074 | 2/1985 | Ray et al. | 623/1 |
| 4,501,263 | 2/1985 | Harbuck | |
| 4,503,568 | 3/1985 | Madras | |
| 5,156,619 | 10/1992 | Ehrenfeld | |
| 5,323,789 | 6/1994 | Berggren et al. | 128/898 |
| 5,336,256 | 8/1994 | Urry | |
| 5,354,329 | 10/1994 | Whalen | |

FOREIGN PATENT DOCUMENTS

| 269254 | 6/1988 | European Pat. Off. |
| 2666502 | 3/1992 | France |

*Primary Examiner*—David H. Willse
*Attorney, Agent, or Firm*—Cushman, Darby & Cushman IP Group of Pillsbury Madison & Sutro LLP

[57] ABSTRACT

The present invention provides a synthetic vascular prosthesis which is formed by a first tube member and a second tube member. Both tube members have inner flow paths for blood. An end of the second tube member is connected with an outer surface of the first tube member, and the inner flow path of the second tube member is communicated with the inner flow path of the first tube member.

2 Claims, 4 Drawing Sheets

SYNTHETIC VASCULAR PROSTHESIS

BACKGROUND OF THE INVENTION

1. Field of the Invention

The present invention relates to a synthetic vascular prosthesis used to replace or bypass a lesioned portion of an in vivo blood vessel affected by an obstructive or distentive lesion.

2. Prior Art

When an obstructive or distentive lesion is produced in an in vivo blood vessel, surgery may be carried out to bypass or to replace the in vivo blood vessel using a substitute blood vessel. The substitute blood vessel may be either a blood vessel section obtained from a human body or a synthetic vascular prosthesis formed of materials such as polytetrafluoroethylene.

There are two methods for connecting the synthetic vascular prosthesis to the in vivo blood vessel. FIG. 5A shows an end-to-end anastomosis for an end 1a of the in vivo blood vessel 1 and an end 2a of the synthetic vascular prosthesis 2. FIG. 5B shows an end-to-side anastomosis for an outer surface 1b of the in vivo blood vessel 1 and the end 2a of the synthetic vascular prosthesis 2.

In the case of using the end-to-side anastomosis, first, a slit-shaped opening 3 is formed on the outer surface 1b of the in vivo blood vessel 1, as shown in FIG. 6. The end 2a of the synthetic vascular prosthesis 2 is deformed, so as to conform to the slit-shaped opening 3. Then, a circumference of the end 2a is sutured to a circumference of the opening 3. In this suturing procedure, as shown in FIG. 7, both the circumference of the end 2a and the circumference of the opening 3 are normally bent outwardly, so that an inner face of the end 2a and an inner face of the opening 3 are brought into contact with each other. Then, the contact portion is sutured using a suturing thread 4 to complete the end-to-side anastomosis procedure. This inside-to-inside suturing is desirable because the outside of the blood vessel has a property of coagulating blood.

Various lesions in blood vessels may be produced if blood flow in the blood vessels is too rapid or too slow, if break away is generated in the blood flow, or if shearing stress in the blood flow is too large or too small.

Conventional end-to-side anastomosis has a problem in that a cross section of the blood flow path alters abruptly in the region, where the end 2a of the synthetic vascular prosthesis 2 is deformed into a slit-shape, and where the blood flows from the synthetic vascular prosthesis 2 into the in vivo blood vessel 1, so that the blood flow rate and the shearing stress change significantly.

In the case of using the end-to-side anastomosis, the synthetic vascular prosthesis should also be provided with a predetermined cross sectional area, even if it is deformed into a slit-shape. Consequently, this anastomosis method has a problem in that the length of the suturing is increased, because the more the end 2a is deformed, the greater the circumference of the end 2a, for the same predetermined cross sectional area.

Moreover, it is complicated to form a slit-shaped opening on the outer surface of the blood vessel and to bend the circumference of the opening outwardly, so that the procedure has a further problem in that it requires considerable time to complete it.

Furthermore, as the end 2a of the synthetic vascular prosthesis 2 is deformed to be sutured with the in vivo blood vessel 1, additional shearing stress is applied around the connected region of the blood vessel 1, so that the cross sectional shape of the blood vessel 1 may be altered. Thus, a further problem exists in that lesions may be produced in the in vivo blood vessel 1 around the connected region due to the additional shearing stress or the alteration of the cross section.

SUMMARY OF THE INVENTION

The present invention was developed in view of the above-described problems; it has as an object thereof to provide a synthetic vascular prosthesis which minimizes changes in blood flow caused by an anastomosis and improves workability of an anastomosis procedure.

A synthetic vascular prosthesis of the present invention comprises a first tube member and a second tube member, an end of the second tube member being connected to an outer surface of the first tube member. Both the first tube member and the second tube member have inner flow paths through which blood may flow. In the connected region, the flow path of the second tube member communicates with the flow path of the first tube member. That is, an end-to-side anastomosis portion has already been formed in the above-described synthetic vascular prosthesis. Thus, in the case of suturing the synthetic vascular prosthesis to an in vivo blood vessel, first, the lesioned portion of the in vivo blood vessel is cut out, then both ends of the first tube member are sutured to corresponding cut-out ends of the in vivo blood vessel using the end-to-end anastomosis procedure. In this manner, the procedures for forming a slit-shaped opening on the outer surface of the blood vessel, and for bending a circumference of the opening outwardly, are rendered unnecessary. Furthermore, the length of the suturing procedure for the end-to-end anastomosis is shorter than the suturing procedure for the slit-shaped opening. Thus, the anastomosis procedure may be performed more easily, and consequently, improved workability can be obtained.

The second tube member is connected with the first tube member, preferably, in a manner such that a circumference of the end of the second tube member is sutured with a circumference of an opening formed on the outer surface of the first tube member. Because such circumference-to-circumference suturing is used, there is no projection extending from an inner wall of the tube members into the flow path in the region where the blood flows from the first tube member into the second tube member. Thus, blood flow is not obstructed, and consequently changes In the blood flow can be minimized.

Moreover, the second tube member is connected with the first tube member, preferably in a manner such that a cross section of the flow path of the second tube member is substantially the same as a cross section of the flow path of the first tube member around the connected region. In this case, the "cross section" refers to the cross section perpendicular to the flow direction of the blood. In this method, the end of the second tube member is no longer deformed into a slit-shape, so that there is no region having an abrupt cross sectional change. Moreover, as both tube members have substantially the same cross section, there is also no abrupt cross sectional change in the region where the flow path of the second tube member is communicated with the flow path of the first tube member. As described above, the flow path has no abrupt cross sectional change, so that the changes in the blood flow can be minimized.

Furthermore, it is preferable that the first tube member intersects the second tube member at an angle from 20 degrees to 45 degrees. Thus, the blood flows smoothly from the second tube member into the first tube member, and consequently the changes in the blood flow can be minimized.

BRIEF DESCRIPTION OF THE DRAWINGS

FIG. 3A shows the in vivo blood vessel with an excised portion, and FIG. 3B shows the synthetic vascular prosthesis connected with the blood vessel.

FIG. 5A shows an end-to-end anastomosis, and FIG. 5B shows an end-to-side anastomosis.

DETAILED DESCRIPTION OF THE PREFERRED EMBODIMENTS OF THE INVENTION

Referring to FIG. 1 to FIG. 4, preferred embodiments according to this invention will be described in detail. A synthetic vascular prosthesis of this invention is formed from connecting two tube members, each of which works as a synthetic vascular prosthesis individually. In general, this tube member for a synthetic vascular prosthesis is produced as a molded product made of suitable materials such as polytetrafluoroethylene, or is formed by weaving fibers of suitable materials.

Figure 1:
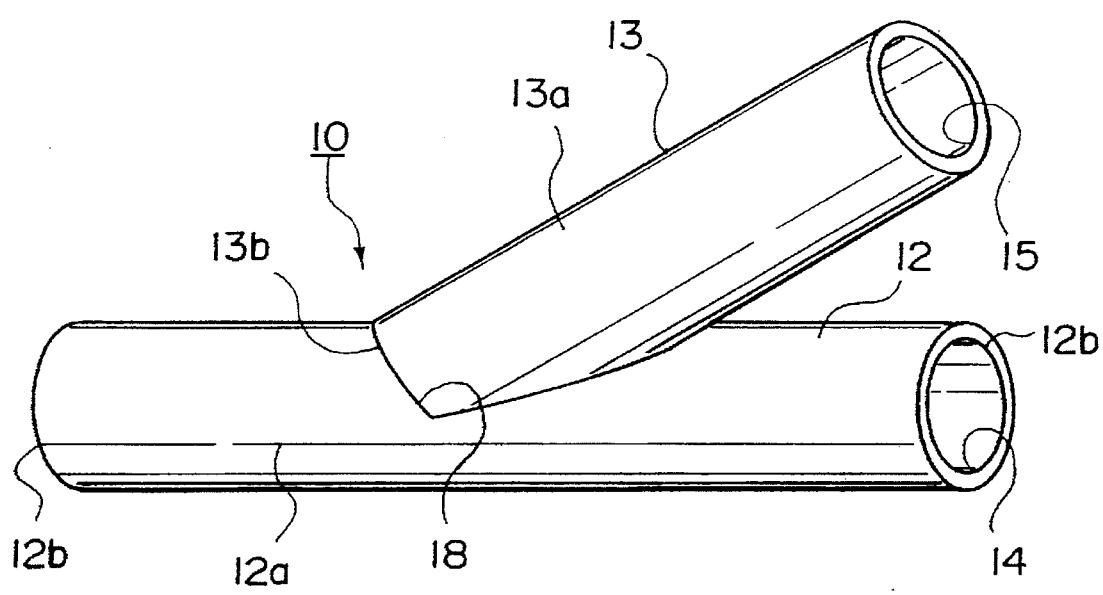
FIG. 1 is a perspective view showing one embodiment of a synthetic vascular prosthesis of this invention.

As shown in FIG. 1, a synthetic vascular prosthesis 10 comprises a first tube member 12 and a second tube member 13. Both of the tube members include inner flow paths 14 and 15 respectively, through which blood flows. Cross sections of both tube members 12 and 13 have similar configurations and are formed into a substantially circular shape.

Figure 2:
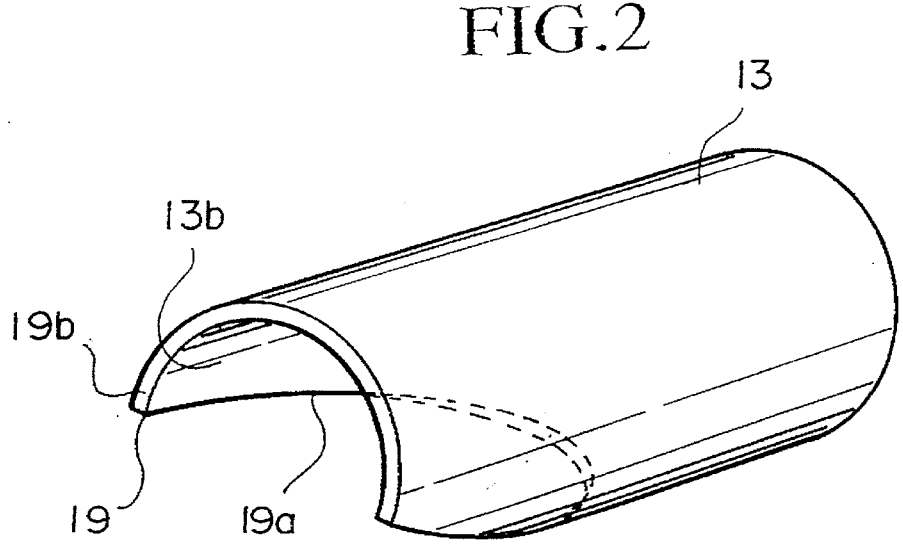
FIG. 2 is a perspective view showing a second tube member of the synthetic vascular prosthesis.

An opening 18 is formed on an outer surface 12a of the first tube member 12. A circumference of an end 13b of the tube member 13 is connected with a circumference of the opening 18 uniformly to close the, opening 18, in a manner such that the tube member 13 should intersect tube member 12 at an angle of about 30 degrees. In this case, as shown in FIG. 2, a cut-out edge 19a is formed in the tube member 13, and a circumference 19 of the end 13b of the tube member 13 consists of the cut-out edge 19a and a side edge 19b. The opening 18 is formed into a similar configuration as the circumference 19, in order to minimize deformation of the tube member 13 around the region connected with the tube member 12. In the connection of both circumferences, using the same method as the above-mentioned conventional end-to-side anastomosis, both of circumferences are bent outwardly, and both inner faces are brought into contact with each other. Then, the contact region is bonded by means such as suturing, adhesion, and welding. Both of tube members 12 and 13 of the synthetic vascular prosthesis 10 are formed longer than the anticipated necessary size for the anastomosis procedure. Thus, both of tube members 12 and 13 can be cut according to working conditions, so that the synthetic vascular prosthesis of proper size can be used in the anastomosis procedure.

Figure 3A:
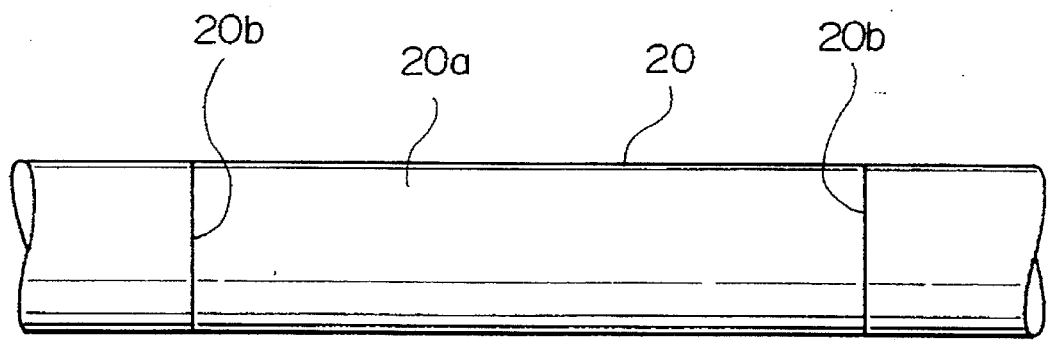
FIGS. 3A and 3B are side views showing anastomosis procedures using the synthetic vascular prosthesis of this invention; in particular.
Figure 3B:
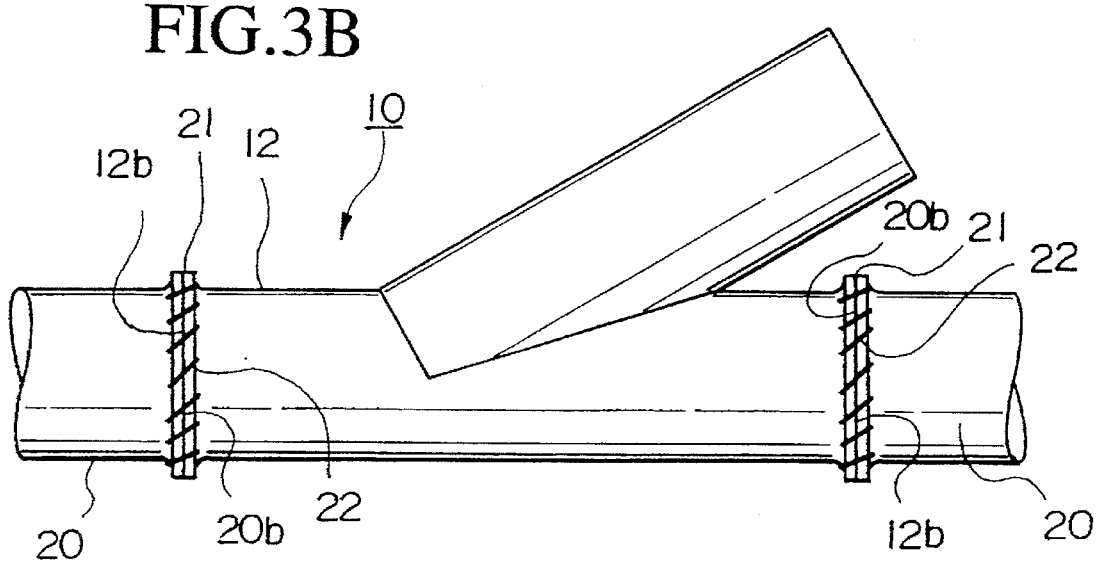

Next, the anastomosis procedure using the synthetic vascular prosthesis 10 of this invention is described. First, the tube member 12 and the tube member 13 are cut to proper sizes according to working conditions. Then, as shown in FIG. 3A, a lesioned portion 20a of an in vivo blood vessel 20 is excised out, so that two ends 20b and 20b of the blood vessel 20 are formed. Then, as shown in FIG. 3B, both ends 12b and 12b of the tube member 12 are sutured with corresponding ends 20b and 20b of the blood vessel 20 respectively using the end-to-end anastomosis procedure. In this case, using the same method as the above-mentioned end-to-side anastomosis, an inner face of the end 12b and an inner face of the end 20b are brought into contact with each other, and contact portions 21 are sutured using a suturing thread 22.

Using the synthetic vascular prosthesis 10 of this invention, deformation of the tube member 13, around the connected region with the tube member 12, can be minimized. Moreover, the tube member 13 has a similar cross section to the tube member 12 around the connected region. Further, the circumference of the end 13b of the tube member 13 is connected with the circumference of the opening 18 of the tube member 12, so that there is no projection extending from inner faces of the tube members 12 and 13 into the flow paths 14 and 15. Thus, there is no portion having abrupt cross sectional change in the flow path 14 and 15, so that the changes in the blood flow can be minimized.

In the case of connecting the tube member 13 with the tube member 12, too small a cross angle would lead to a longer bonding distance for the connected region. In contrast, too large an intersection angle would lead to large directional change of blood flow from the flow path 15 into the flow path 14, so that turbulent flow is caused in the blood flow. Thus, the intersection angle is preferably from 20 degrees to 40 degrees. The cross angle of the synthetic vascular prosthesis 10 of this embodiment is 30 degrees, and is within the above-mentioned angle range, so that the blood flows smoothly from the flow path 15 into the flow path 14, and consequently the changes in the blood flow can be minimized.

As the synthetic vascular prosthesis 10 can be sutured with the in vivo blood vessel 20 by using the end-to-end anastomosis procedure, the suturing length is reduced compared with the end-to-side anastomosis which has the slit-shaped sutured region, because both anastomosis procedures should have the same predetermined cross sectional area for the flow path. Moreover, procedures for forming a slit-shaped opening on the outer surface of the in vivo blood vessel 20, and for bending the circumference of the opening outwardly, are rendered unnecessary. Thus, the anastomosis procedure can be easier to perform, and consequently, improved workability can be obtained.

Figure 4:
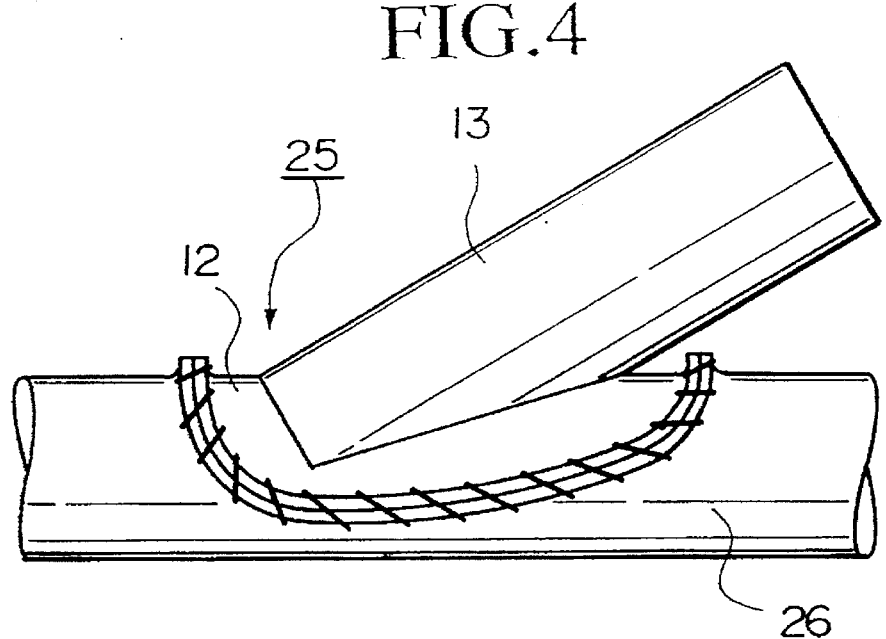
FIG. 4 is a side view showing another anastomosis procedure using the synthetic vascular prosthesis of this invention.
Figure 5A:
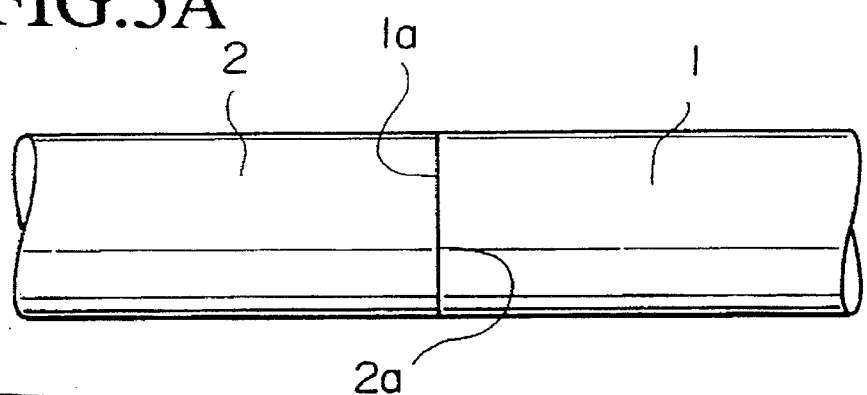
FIGS. 5A and 5B are side views showing conventional anastomosis methods; in particular.
Figure 5B:
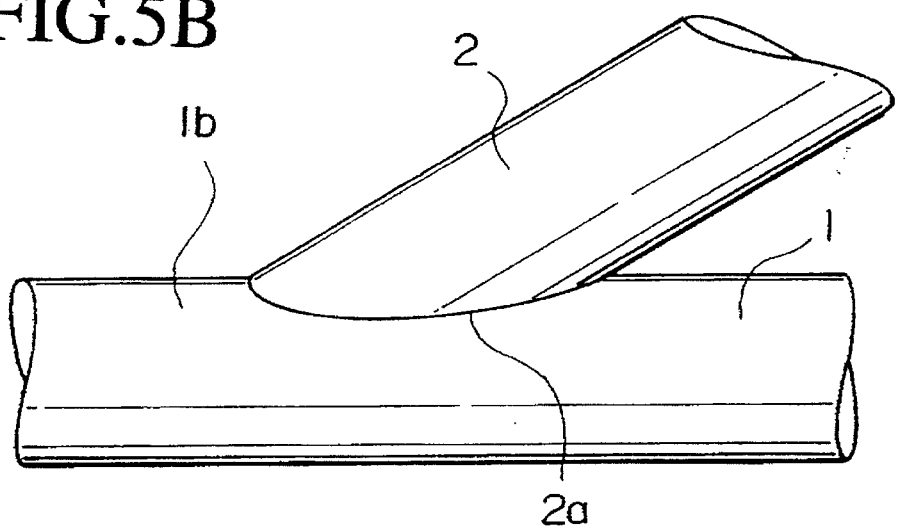
Figure 6:
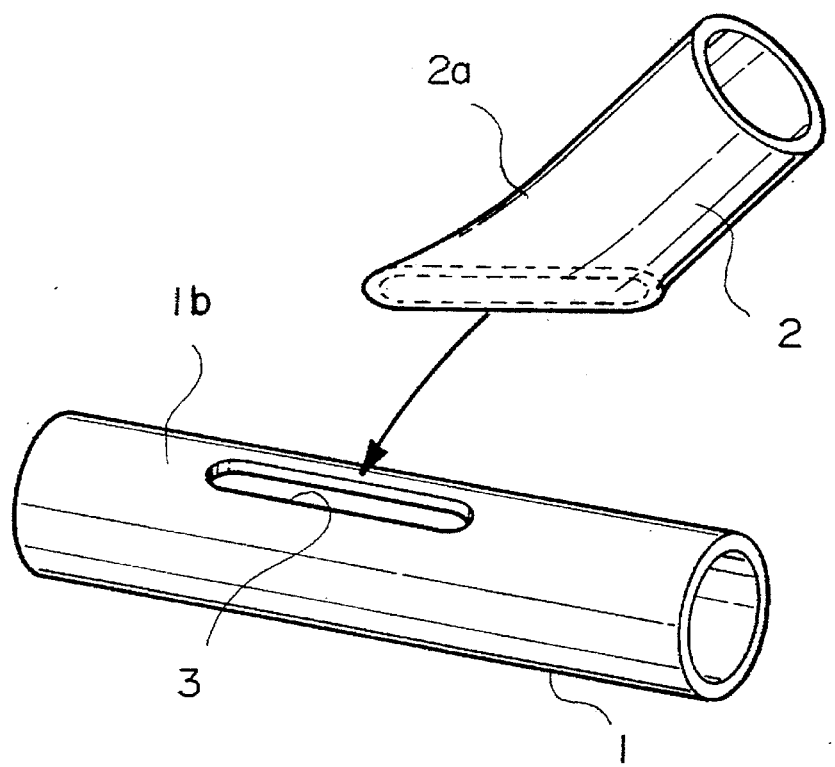
FIG. 6 is a perspective view showing the conventional end-to-side anastomosis procedure.
Figure 7:
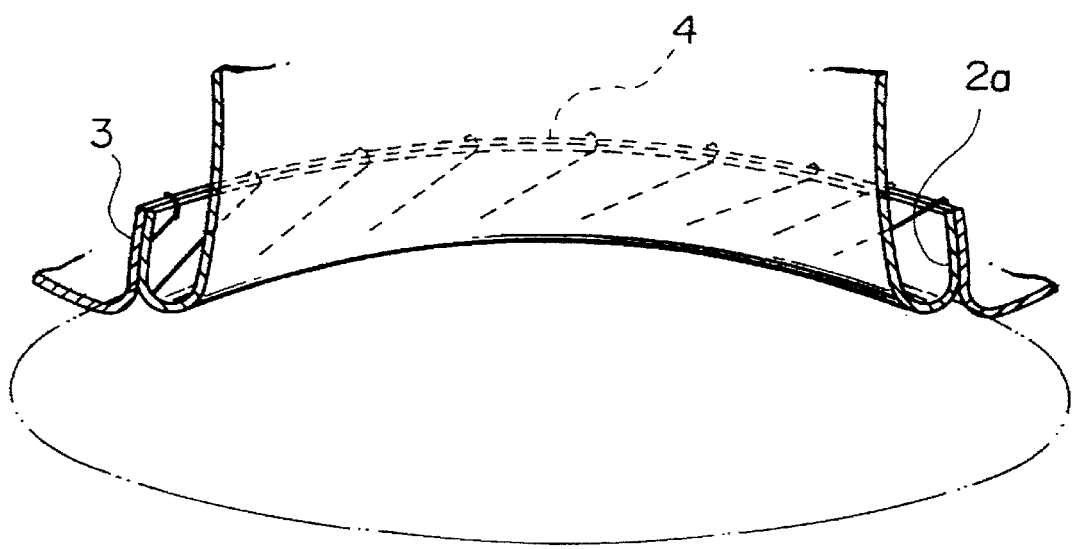
FIG. 7 is a perspective view showing a sutured portion formed in the end-to-side anastomosis procedure.

FIG. 4 shows another embodiment of the synthetic vascular prosthesis 10 of this invention. A synthetic vascular prosthesis 25 is formed, which has a configuration shown in the figure, from the synthetic vascular prosthesis 10, by cutting around the connected region of the tube member 12. In the case of using the synthetic vascular prosthesis 25 for an anastomosis with an in vivo blood vessel 26, the end-to-side anastomosis procedure is used. The anastomosis using the synthetic vascular prosthesis 25 has the same effect as the anastomosis using the synthetic vascular prosthesis 10, in that there is a reduction in the changes in the blood flow.

Although preferred embodiments of the present invention have been described, it is to be understood that the invention is not limited to those precise embodiments, and that further changes and modifications may be made by one skilled in the art without departing from the scope of the invention. For example, while cross sections of the first tube member and the second tube member are uniform along longitudinal axes of the tubes in the above-mentioned embodiments, it is possible to adopt a tube member in which the flow path has a gradually increasing or decreasing diameter along a longitudinal axis, in order to conform to the size of the connected blood vessel.

Further, while the circumference of the end of the second tube member is connected with the circumference of the opening of the first tube member in the above-mentioned embodiments, it is possible to adopt a second tube member, which has a flange portion extending outwardly from an end of the second tube member. This flange portion is formed to be larger than the opening of the first tube member. In the case of forming a combined synthetic vascular prosthesis, first, the flange portion is inserted into the first tube member through the opening. Then, a sealing procedure is carried out between the flange portion and an inner wall of the first tube member by means of suturing, adhesion, etc., so that the second tube member is connected with the first tube member with a seal.

What is claimed is:

1. A synthetic vascular prosthesis comprising:

a first synthetic vascular tube member defining an inner path for blood flow; and a second synthetic tube member defining an inner path for blood flow, said second tube member being constructed separately from said first tube member, a circumference of one end of said second tube member being connected with a circumference of an opening formed on an outer surface of said first tube member, said circumference of said one end of said second tube member consisting of a side edge formed in a direction substantially perpendicular to an axis of said second tube member and a cut-out edge extending from said side edge in a direction inclined to both the axis of said second tube member and said side edge, said circumference of said opening of said first tube member having a substantially identical shape as said circumference of said one end of said second tube member.

2. The synthetic vascular prosthesis according to claim 1, wherein the circumference of the opening of the first tube member and the circumference of the one end of the second tube member are both bent outwardly and an inner face of the first tube member adjacent the opening of the first tube member is bonded to an inner face of the second tube member adjacent the one end of the second tube member.

\* \* \* \* \*